United States Patent [19]

Silva

[11] Patent Number: 4,571,425

[45] Date of Patent: Feb. 18, 1986

[54] METHOD FOR MAKING AROMATIC BIS(ETHER ANHYDRIDE)

[75] Inventor: James M. Silva, Clifton Park, N.Y.

[73] Assignee: General Electric Company, Schenectady, N.Y.

[21] Appl. No.: 701,833

[22] Filed: Feb. 14, 1985

[51] Int. Cl.$^4$ ............................................ C07D 307/89
[52] U.S. Cl. ...................................... 549/241; 548/454
[58] Field of Search ......................... 549/241; 548/454

[56] References Cited

U.S. PATENT DOCUMENTS

| | | | |
|---|---|---|---|
| 3,879,428 | 4/1975 | Heath et al. | 549/241 |
| 4,116,980 | 9/1978 | Webb | 549/241 |
| 4,340,545 | 7/1982 | Webb et al. | 549/241 |

OTHER PUBLICATIONS

Distillation with Chemical Reaction Studies in a Six-tray Sieve Column, Jeffreys et al., Chimie et Industrie-Genie Chimique, vol. 101, No. 8, 4/69, pp. 1111–1117.

Countercurrent Equilibrium Stage Separation with Reaction, Nelson, AIChE Journal, vol. 17, No. 5, 9/71, pp. 1043–1049.

*Primary Examiner*—Richard L. Raymond
*Attorney, Agent, or Firm*—William A. Teoli; James C. Davis, Jr.; James Magee, Jr.

[57] ABSTRACT

A method is provided for making aromatic bis(ether anhydrides) by effecting an exchange reaction between aromatic bis(ether imide) and phthalic anhydride in the presence of water and an exchange catalyst. The separation and recovery of phthalimide and aromatic bis(ether anhydride) is achieved in a stripper-reactor using a vaporous mixture of water and the exchange catalyst.

4 Claims, 1 Drawing Figure

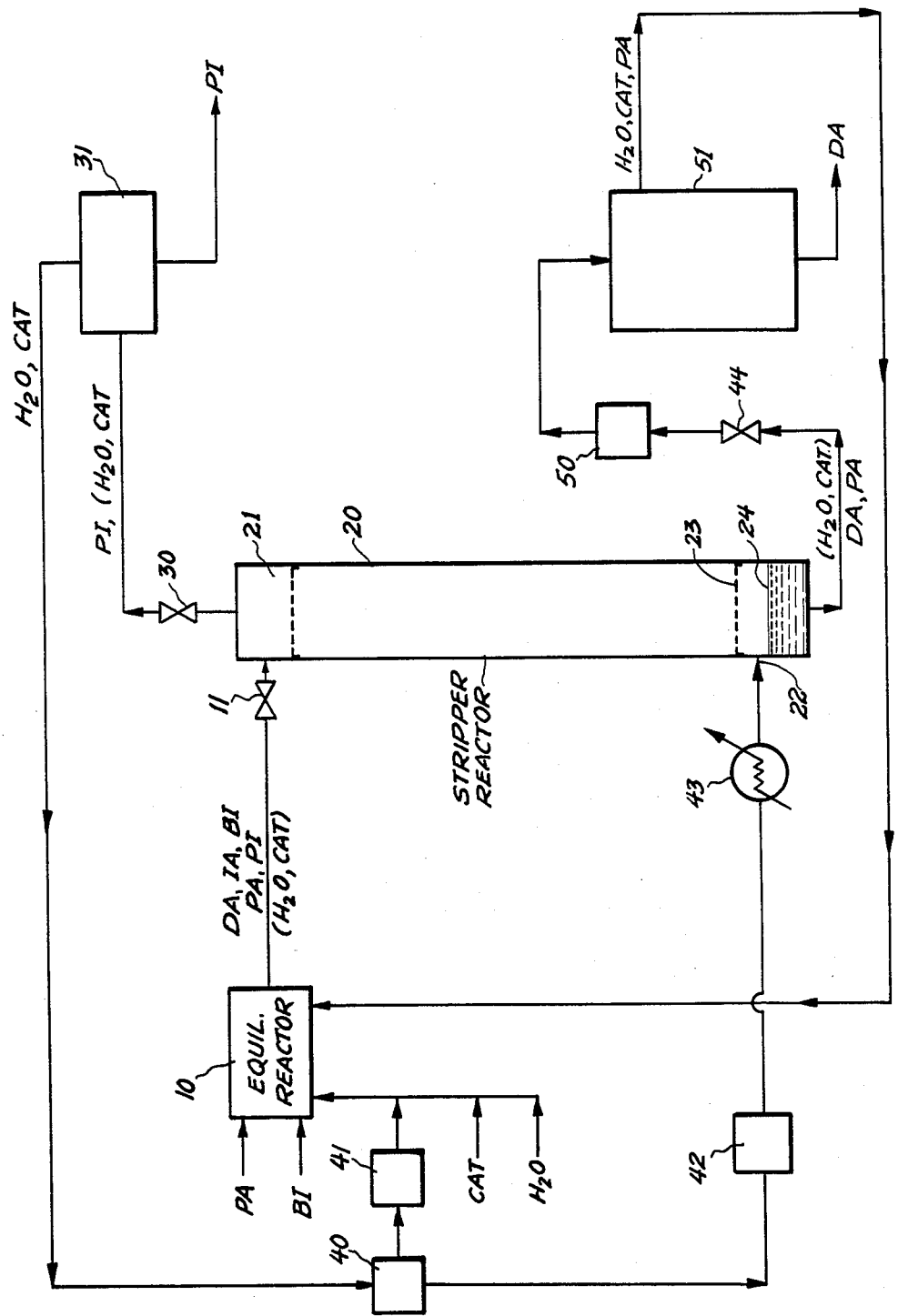

METHOD FOR MAKING AROMATIC BIS(ETHER ANHYDRIDE)

BACKGROUND OF THE INVENTION

As shown by Webb et al. U.S. Pat. No. 4,340,545, assigned to the same assignee as the present invention and incorporated herein by reference, aromatic bis(ether anhydrides) were made by effecting an imide-anhydride exchange between aromatic bis(ether-N-organophthalimide) and phthalic anhydride in the presence of an imide-anhydride exchange catalyst and water. Recovery of the aromatic bis(ether anhydride) was achieved by extracting the aqueous imide-anhydride exchange reaction mixture with an inert organic solvent, such as toluene. Although valuable results have been achieved with the practice of the aforementioned method of Webb at al., it would be desirable to recover aromatic bis-(ether anhydride) without the employment of an organic solvent.

The present invention is based on the discovery that aromatic bis(ether anhydride) can be made by an imide-anhydride exchange reaction between aromatic bisimide and phthalic anhydride in the presence of an imide-anhydride exchange catalyst and water followed by the use of a vaporous mixture of water and the imide-anhydride exchange catalyst in a stripper-reactor, without the employment of an organic solvent.

STATEMENT OF THE INVENTION

There is provided by the present invention a process for making aromatic bis(ether anhydride) which comprises (1) effecting an imide-anhydride exchange in an equilibration reactor between aromatic bisimide and phthalic anhydride in the presence of an imide-anhydride exchange catalyst and water resulting in the production of an equilibration mixture comprising an aromatic bis(ether anydride) and phthalimide melt, (2) feeding the equilibration mixture of (1) to a stripper-reactor, (3) effecting the separation of phthalimide from aromatic bis(ether anhydride) in the stripper-reactor with a mixture of water and exchange catalyst maintained in the vaporous state at a temperature of from about 150° C. to 250° C., (4) recovering the phthalimide from (3) as an aqueous mixture consisting essentially of phthalimide, water and exchange catalyst, (5) recovering phthalimide from the mixture of (4) and recycling water and exchange catalyst to the equilibration reactor and the stripper-reactor, (6) recovering a mixture comprising aromatic bis-(ether anhydride) from the stripper-reactor as an aqueous melt, (7) conveying the aqueous melt of (6) to a separator to provide for the recovery of the aromatic bis(ether anhydride) and (8) recycling the resulting mixture comprising water and exchange catalyst to the equilibration reactor.

Some of the aromatic bis(ether anhydride)s which can be made in the practice of the method of the present invention are included by the formula

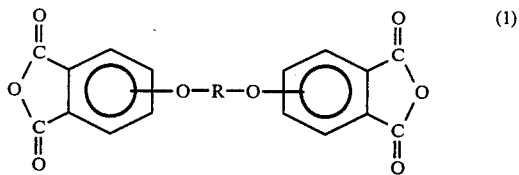

where R is a $C_{(6-30)}$ divalent aromatic organic radical. Radicals included by R are more particularly

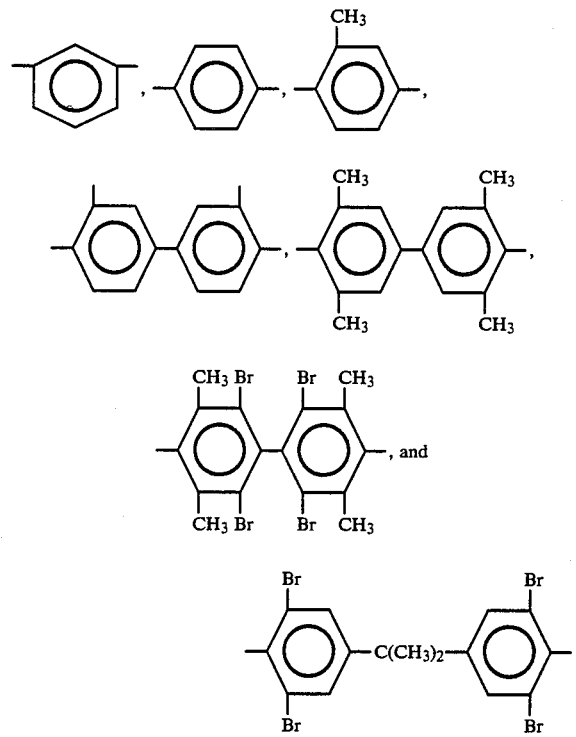

and divalent organic radicals of the general formula

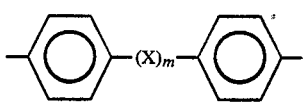

where X is a member selected from the class consisting of divalent radicals of the formulas,

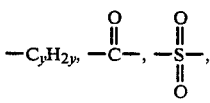

—O—, and —S—, where m is 0 or 1, and y is a whole number from 1 to 5.

The aromatic bis(ether phthalic anhydride) of formula (1) can be made by effecting reaction between an aqueous mixture of phthalic acid and imide anhydride exchange catalyst, such as a $C_{(1-8)}$ trialkylamine, for example, triethylamine, with molten aromatic bis(ether phthalimide) of the formula

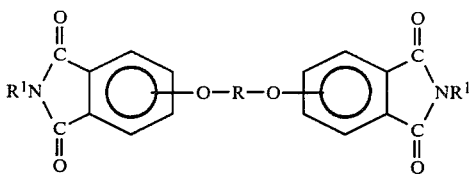

(2)

where $R^1$ is a monovalent organo radical selected from the class consisting of $C_{(1-8)}$ alkyl radicals and $C_{(6-13)}$ aromatic radicals.

Radicals included by $R^1$ are, for example, phenyl, tolyl, xylyl, naphthyl, chlorophenyl, bromonaphthyl, etc., and alkyl radicals, such as methyl, ethyl, etc.

As shown in U.S. Pat. No. 3,879,428, the aromatic bis(ether phthalimide)s of formula (2) can be made by effecting reaction between phthalimides of the formula,

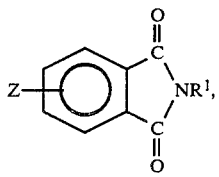

(3)

where Z is a radical selected from the class consisting of nitro, halo, fluoro, bromo, etc., and $R^1$ is as previously defined, and alkali diphenoxide of the formula,

M—O—R—O—M, (4)

where R is as previously defined, and M is a metal ion of an alkalide metal selected from the class consisting of sodium, potassium, lithium, etc.

Included by the alkali diphenoxides of formula (4), are sodium and potassium salts of the following dihydric phenols,
2,2-bis(2-hydroxypheny)propane;
2,4'-dihydroxydiphenylmethane;
bis-(2-hydroxyphenyl)methane;
2,2-bis(4-hydroxyphenyl)propane, hereinafter identified as "Bisphenol-A" or "BPA";
1,1-bis(4-hydroxyphenyl)ethane;
1,1-bis(4-hydroxyphenyl)propane;
2,2-bis(4-hydroxyphenyl)pentane;
3,3-bis(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4-dihydroxydiphenylsulfone;
4,4'-dihydroxydiphenyl sulfoxide;
4,4-dihydroxydiphenyl sulfoxide;
4,4'-dihydroxydiphenyl sulfide; hydroquinone; resorcinol;
3,4'-dihydroxidiphenylmethane;
3,3'-dihydroxybenzophenone;
4,4'-dihydroxybenzophenone; and
4,4'-dihydroxydiphenylether.

A more complete understanding of the practice of the method of the present invention can be obtained by reference to the drawing.

There is shown a schematic of an equilibration reactor joined to a stripper-reactor and means for recovering phthalimide and aromatic bisanhydride and the recycling of water and imide-anhydride exchange catalyst. In the drawing "DA" is aromatic bis(ether anhydride) of formula (1), "IA" is the corresponding aromatic imide anhydride, "BI" is aromatic bis(ether phthalimide), "PA" is phthalic anhydride, "PI" is phthalimide and "CAT" is imide-anhydride exchange catalyst or triethylamine.

More particularly, there is shown an equilibration reactor at 10 into which molten PA and BI are introduced. Thorough mixing of the molten BI and aqueous PA feed which are maintained at flow rates sufficient to maintain a ratio of about 6 moles of PA per mole of BI can be achieved by passing the feed stream through a mixing zone, not shown, prior to entering the reactor. After a residence of about 10 minutes in the reactor at temperatures at 200° C. to 220° C. and a pressure of from 300 psi to 500 psi, the mixture is then fed into a heated line which passes through a valve at 11 prior to entry into the stripper-reactor at 20.

The stripper-reactor at 20 is a packed or plate column. The stripper-reactor has a liquid distributor at 21. The stripper-reactor is maintained at a temperature of about 150°–250° C. and a pressure sufficient to allow for the collection of the DA melt at 24 while continuously passing a vaporous mixture of the CAT and water which is introduced at 22 and allowed to pass through the perforations of a support plate at 23.

A vaporous mixture of PI, water and CAT is conveyed through a pressure adjusting valve at 30 to a separator at 31 to provide for the recovery of the PI and the recycling of a mixture of water and CAT to a stream splitter at 40. The stream splitter feeds part of the recycle stream to a pump at 41 prior to being recycled to the equilibration reactor. The balance of the recycled aqueous CAT stream is fed to a pump at 42 and thereafter to a heat exchanger at 43 and then conveyed in vaporous form to the stripper-reactor at 22.

The DA melt 24 is conveyed through a liquid level control valve at 44 to a holding tank at 50 prior to being fed into a separator at 51. Preferably, the separator at 51 is a thin film evaporator or a wiped film or rotary evaporator. DA is then collected as a melt from the separator. A mixture of water, CAT and PA can be recycled to the equilibration.

In order that those skilled in the art will be better able to practice the method of the present invention, the following example is given by way of illustration and not by way of limitation. All parts are by weight.

EXAMPLE 1

There was added to an autoclave, a mixture of 2,2-bis[4-(3,4-dicarboxyphenoxy)phenyl]propane bis-N-methylimide (546 parts), phthalic anhydride (925 parts), water (1200 parts), and triethylamine (1232 parts). The autoclave was sealed and heated with stirring to 200° C. After the mixture had been heated for 1 hour at 200° C., the autoclave was allowed to cool and then it was opened. There was obtained an equilibration reaction product consisting of 2,2-bis[4-(3,4-dicarboxyphenoxy)-phenyl]propane bis-N-methylimide, 2,2-bis[4-(3,4-dicarboxyphenoxy)phenyl]propane N-methyl monoimide anhydride, and 2,2-bis[4-(3,4-dicarboxyphenoxy)-phenyl]propane dianhydride in the proportion 4.313:31.93:60.32 (parts by weight). The product was transferred to a jacketed glass feed tank equipped with a stirrer and a water-cooled condenser. It was maintained in the molten state by circulating hot oil through the jacket. The liquid product was fed to the top of a stripper-reactor via a Hills-McAnna positive displacement pump equipped with heated check valves, a heated barrel, and heated transfer lines.

The stripper-reactor was a 1 inch i.d. type 316 stainless steel tube, 5 feet long packed with 0.16 inch protruded metal packing, "Propak", which was manufactured by Scientific Development Company, State College, PA. The stripper-reactor was heated by circulating hot oil through its jacket, which was a 5 foot tube having a 2.5 inch o.d. Pressure was controlled by throttling the overheads vapor product flow rate. A pneumatic pressure controller (Fisher Controls Corp. Model 4160) sensed the stripper-reactor overhead pressure and manipulated a pneumatic valve (Research Control Valve model 78S, Badger Meter Inc., Tulsa, Okla.). Oil was circulated at 210° C. and the overhead pressure was maintained at 150 psig. Bottoms product accumulated in a heated sight glass, which was periodically isolated from the system and drained.

Liquid equilibration reaction product was metered into the top of the stripper-reactor at 1 gm/min and strip gas (1 part water 1 part triethylamine) was metered at 11.8 gm/min as a liquid into a heater/vaporizer and then into the bottom of the stripper-reactor as a vapor.

The stripper-reactor was operated continuously for a period of 4.5 hours under these operating conditions. The bottoms product was stripped of phthalic anhydride, water, and triethylamine in a rotary evaporator and was analyzed by liquid chromatography. The bottoms product was found to contain 99 parts 2,2-bis[4-(3,4-dicarboxyphenoxy)phenyl]propane dianhydride and 1 part 2,2-bis[4-(3,4-dicarboxyphenoxy)phenyl]propane N-methyl monoimide anhydride. The amount of bisimide remaining in the bottom product was negligible. The bottoms product was also analyzed by gas chromatography and found to be free of phthalimide. The overhead product was condensed and the water and triethylamine were removed by rotary evaporation. The overhead product after evaporation of the water and triethylamine was found by gas chromatography to contain 98 wt% phthalimide and 2 wt% phthalic anhydride.

Although the above example is directed to only a few of the very many variables which can be utilized in the practice of the method of the present invention, it should be understood that the present invention is directed to the use of a much broader variety of aromatic bisimide, aromatic bisanhydride and equilibration catalyst as shown in the description preceding this example.

What I claim as new and desire to secure by Letters Patent of the United States is:

1. A process for making aromatic bis(ether anhydride) which comprises
   (1) effecting an imide-anhydride exchange in an equilibration reactor between aromatic bisimide and phthalic anhydride in the presence of an imide-anhydride exchange catalyst and water resulting in the production of an equilibration mixture comprising an aromatic bis(ether anhydride) and phthalimide melt,
   (2) feeding the equilibration mixture of (1) to a stripper-reactor,
   (3) effecting the separation of phthalimide from aromatic bis(ether anhydride) in the stripper-reactor with a mixture of water and exchange catalyst maintained in the vaporous state at a temperature of from about 150° C. to 250° C.,
   (4) recovering the phthalimide from (3) as an aqueous mixture consisting essentially of phthalimide, water and exchange catalyst,
   (5) recovering phthalimide from the mixture of (4) and recycling water and exchange catalyst to the equilibration reactor and the stripper-reactor,
   (6) recovering a mixture comprising aromatic bis(ether anhydride) from the stripper-reactor as an aqueous melt,
   (7) conveying the aqueous melt of (6) to a separator selected from the class consisting of a thin film evaporator, a wiped film evaporator and a rotary evaporator to provide for the recovery of the aromatic bis(ether anhydride) and
   (8) recycling the resulting mixture comprising water, phthalic anhydride and exchange catalyst to the equilibration reactor.

2. A process of claim 1 where the aromatic bis(ether phthalimide) is 2,2-bis[4-(3,4-dicarboxyphenoxy)phenyl]propane bis-N-methylimide.

3. A process of claim 1 where the aromatic bis(ether phthalic anhydride) is a mixture of 2,2-bis[4-(3,4-dicarboxyphenoxy)phenyl]propane dianhydride and 2,2-bis[4-(3,4-dicarboxyphenoxy)phenyl]propane-N-methylmonoimide anhydride.

4. A process of claim 1 where the imide anhydride exchange catalyst is triethylamine.

* * * * *